US009271864B2

(12) United States Patent
Feinstein

(10) Patent No.: US 9,271,864 B2
(45) Date of Patent: Mar. 1, 2016

(54) ORTHOSIS FOR RANGE OF MOTION, MUSCULAR AND NEUROLOGIC REHABILITATION OF THE LOWER EXTREMITIES

(75) Inventor: Peter A. Feinstein, Shavertown, PA (US)

(73) Assignee: FEINSTEIN PATENTS LLC, Shavertown, PA (US)

( * ) Notice: Subject to any disclaimer, the term of this patent is extended or adjusted under 35 U.S.C. 154(b) by 1080 days.

(21) Appl. No.: 13/352,476

(22) Filed: Jan. 18, 2012

(65) Prior Publication Data

US 2013/0085420 A1 Apr. 4, 2013

(51) Int. Cl.
*A61H 1/02* (2006.01)
*A61N 1/04* (2006.01)
(Continued)

(52) U.S. Cl.
CPC ................ *A61F 7/007* (2013.01); *A61H 1/024* (2013.01); *A61N 1/0456* (2013.01); *A61N 1/0468* (2013.01); *A61F 2007/0029* (2013.01); *A61F 2007/0039* (2013.01); *A61F 2007/0096* (2013.01); *A61H 1/0244* (2013.01); *A61H 9/0078* (2013.01); *A61H 2201/0207* (2013.01); *A61H 2201/0214* (2013.01); *A61H 2201/0228* (2013.01); *A61H 2201/10* (2013.01); *A61H 2201/1215* (2013.01); *A61H 2201/149* (2013.01); *A61H 2201/165* (2013.01); *A61H 2201/1642* (2013.01);
(Continued)

(58) Field of Classification Search
CPC ... A61N 1/04; A61N 1/0456; A61N 1/36003; A61N 1/36021; A61N 1/36103; A61N 1/36135; A61N 1/18; A61H 2230/25; A61H 2201/10; A61H 2230/50; A61H 1/02
USPC ........ 607/46, 48, 49, 3; 601/5, 15, 23, 27, 29, 601/33–35; 600/301, 554–555, 557, 454
See application file for complete search history.

(56) References Cited

U.S. PATENT DOCUMENTS 4,509,509 A * 4/1985 Bouvet et al. ................... 601/15
4,520,827 A * 6/1985 Wright et al. .................. 607/48
(Continued)

OTHER PUBLICATIONS

International Search Report & Written Opinion of the International Searching Authority Application No. PCT/US2012/056205 Completed: Nov. 8, 2012; Mailing Date: Nov. 21, 2012 20 pages.

*Primary Examiner* — Rachel Young
*Assistant Examiner* — Christopher Miller
(74) *Attorney, Agent, or Firm* — St. Onge Steward Johnston & Reens, LLC

(57) ABSTRACT

A non-invasive apparatus for rehabilitating a joint, limb, and muscles of a patient recovering from surgery on the joint, includes a continuous passive motion device having at least one support member for supporting the limb, at least one hinge coupled to the at least one support member, and at least one actuator for providing reciprocating motion of the at least one support member about the at least one hinge, a plurality of electrodes transmitting at least four modalities chosen from a group consisting of functional electrical stimulation (FES), transcutaneous electrical nerve stimulation (TENS), temperature therapy stimulation, deep vein thrombosis (DVT) prophylactic stimulation, venous blood flow monitoring, and pain monitoring, and a control unit controlling the at least one actuator and the plurality of electrodes according to a coordinated sequence of the reciprocating motion and transmission of the at least four modalities.

29 Claims, 9 Drawing Sheets

(51) Int. Cl.
*A61F 7/00* (2006.01)
*A61H 9/00* (2006.01)

(52) U.S. Cl.
CPC ............ *A61H 2201/1664* (2013.01); *A61H 2201/1676* (2013.01); *A61H 2201/5007* (2013.01); *A61H 2201/5035* (2013.01); *A61H 2201/5043* (2013.01); *A61H 2201/5064* (2013.01); *A61H 2201/5082* (2013.01); *A61H 2201/5097* (2013.01); *A61H 2209/00* (2013.01); *A61H 2230/255* (2013.01); *A61H 2230/50* (2013.01)

(56) References Cited

U.S. PATENT DOCUMENTS

| | | | | |
|---|---|---|---|---|
| 4,556,214 | A | 12/1985 | Petrofsky et al. | |
| 4,724,842 | A * | 2/1988 | Charters | 607/48 |
| 4,798,197 | A * | 1/1989 | Nippoldt et al. | 601/34 |
| 4,825,852 | A * | 5/1989 | Genovese et al. | 601/34 |
| 4,989,605 | A * | 2/1991 | Rossen | 607/46 |
| 5,297,540 | A * | 3/1994 | Kaiser | A61H 1/0266 482/79 |
| 5,399,147 | A * | 3/1995 | Kaiser | 601/34 |
| 5,643,331 | A * | 7/1997 | Katz | 607/48 |
| 5,674,262 | A * | 10/1997 | Tumey | 607/48 |
| 6,456,885 | B1 * | 9/2002 | Shiba et al. | 607/48 |
| 6,564,103 | B2 * | 5/2003 | Fischer et al. | 607/59 |
| 6,599,255 | B2 * | 7/2003 | Zhang | 600/587 |
| 6,701,189 | B2 * | 3/2004 | Fang | A61N 1/08 607/39 |
| 6,725,094 | B2 * | 4/2004 | Saberski | 607/46 |
| 7,260,420 | B2 * | 8/2007 | Patino et al. | 455/567 |
| 7,353,064 | B2 | 4/2008 | Gliner et al. | |
| 7,381,192 | B2 | 6/2008 | Brodard et al. | |
| 7,540,877 | B2 * | 6/2009 | Emsky | 606/242 |
| 7,783,348 | B2 * | 8/2010 | Gill | A61F 7/007 600/15 |
| 7,901,368 | B2 | 3/2011 | Flaherty et al. | |
| 2004/0030270 | A1 | 2/2004 | Johnson | |
| 2004/0127954 | A1 * | 7/2004 | McDonald, III | 607/48 |
| 2004/0230253 | A1 * | 11/2004 | Sakagami et al. | 607/48 |
| 2004/0254624 | A1 * | 12/2004 | Johnson | 607/149 |
| 2005/0273022 | A1 * | 12/2005 | Diaz et al. | 601/5 |
| 2005/0278001 | A1 * | 12/2005 | Qin | A61N 1/37247 607/48 |
| 2005/0283204 | A1 * | 12/2005 | Buhlmann | A61B 5/1107 607/48 |
| 2006/0204532 | A1 | 9/2006 | John | |
| 2007/0033068 | A1 | 2/2007 | Rao et al. | |
| 2007/0270917 | A1 | 11/2007 | Nachum | |
| 2008/0140154 | A1 | 6/2008 | Loeb et al. | |
| 2008/0255480 | A1 * | 10/2008 | Lau | 601/15 |
| 2009/0036799 | A1 * | 2/2009 | Sandhu et al. | 600/587 |
| 2009/0118790 | A1 * | 5/2009 | Van Herk | 607/48 |
| 2009/0234262 | A1 * | 9/2009 | Reid et al. | 601/152 |
| 2009/0275868 | A1 * | 11/2009 | Steingart | A61H 1/024 601/34 |
| 2009/0287264 | A1 * | 11/2009 | Paret | A61N 1/36021 607/3 |
| 2009/0326602 | A1 | 12/2009 | Glukhovsky et al. | |
| 2010/0057149 | A1 * | 3/2010 | Fahey | 607/3 |
| 2010/0217349 | A1 * | 8/2010 | Fahey | 607/48 |
| 2010/0268130 | A1 * | 10/2010 | Khan | 601/46 |
| 2011/0021930 | A1 | 1/2011 | Mazzeo et al. | |
| 2011/0040215 | A1 * | 2/2011 | Knoll | 601/34 |
| 2011/0077560 | A1 | 3/2011 | Jacofsky et al. | |
| 2011/0082517 | A1 * | 4/2011 | Brezel et al. | 607/48 |
| 2011/0208097 | A1 | 8/2011 | Farese et al. | |
| 2012/0226330 | A1 * | 9/2012 | Kolen et al. | 607/48 |

\* cited by examiner

ORTHOSIS FOR RANGE OF MOTION, MUSCULAR AND NEUROLOGIC REHABILITATION OF THE LOWER EXTREMITIES

CROSS-REFERENCE TO RELATED APPLICATIONS

The present Application claims the benefit, under 35 U.S.C. §119(e), of U.S. Provisional Patent Application No. 61/542,999, filed on Oct. 4, 2011, the content of which is incorporated herein by reference.

FIELD OF THE INVENTION

The invention relates to a rehabilitation device and more specifically to a continuous passive motion device capable of providing non-invasive treatment of limbs to facilitate a return of function by restoring range of motion, controlling pain, and stimulating bodily parts, such as muscles, involved in the return of function.

BACKGROUND OF THE INVENTION

After an invasive surgical operation on a joint (e.g. total knee replacement, total hip replacement, anterior cruciate ligament reconstruction), the joint and surrounding bodily parts are often left in a weakened state, requiring immediate rehabilitation. For patients recovering from extensive joint surgery, any attempt at joint motion causes extreme pain. Consequently, patients tend to avoid substantial movement of the limb. This "immobilization" allows the tissue around the joint to become stiff and for scar tissue to form. These undesirable effects lead to limited range of motion in the joint and prolong physical therapy before the joint and limb regain substantial range of motion, neurological function and muscle function. If full range of motion of the joint and limb is not achieved in the immediate or early postoperative period, then the full range of motion may never be recovered.

Another complication that occurs during the postoperative period following surgery on a patient's joint is deep vein thrombosis (DVT). DVT is the formation of blood clots in a deep vein of the patient's limb, which can block blood flow and cause swelling and pain. DVT becomes most serious when a portion of the clot dislodges, travels through the bloodstream to the lungs or brain, and blocks blood flow therein. Several methods of preventing or limiting the chances of developing DVT include the application of pressure to the limb or periodic movement of the limb to promote increased blood flow in the veins. With greater blood flow circulation, clots are less likely to occur.

Continuous passive motion (CPM) devices are often used during early phases of postoperative rehabilitation to provide passive motion to the treated joint and limb, to control postoperative pain, and reduce inflammation. Typical CPM devices continuously move a patient's limb and joint through a predetermined range of motion without exertion by the patient. The passive motion acts to pump blood and edema fluid away from the joint and surrounding tissue. As a result, CPM devices reduce joint stiffness and improve venous blood flow. Despite their therapeutic benefits, these devices fail to produce a complete range of motion in the patient's limb because the muscles therein may not fully extend and contract. Further, CPM devices have shown only limited effectiveness on DVT prevention. In order to overcome these shortcomings and provide a more comprehensive therapeutic treatment, other modalities or forms of stimulation are incorporated with the CPM devices. For instance, to increase a patient's chances of regaining full range of motion, neuromuscular stimulation (NMS) (e.g. functional electrical stimulation) can be combined with the CPM device. This electrophysical modality transmits electrical impulses to the muscles to effect total joint extension and contraction. Alternatively, a CPM device can be combined with a prophylactic therapy to hinder DVT development. Therefore, CPM devices that simultaneously provide passive motion and other stimulating modalities improve the patient's likelihood of regaining full range of motion in the joint and limb without postoperative complications and excessive pain.

Some CPM devices have incorporated an NMS modality to promote range of motion in the limb. For example, U.S. Pat. No. 4,520,827 to Wright et al. discloses a rehab apparatus comprising a CPM unit for supporting a patient's leg through a range of motion, a drive means for moving the leg through the range of motion, and a NMS means for applying electrical stimulation to a muscle in the leg. The rehab apparatus further includes a controller for managing the operation of the CPM unit, drive means, and NMS means. In particular, the controller stops the drive means when the CPM unit is disposed in an extended position and initiates muscle stimulation for a time period in which the CPM unit remains stationary. However, the controller does not allow for varying the sequence or order of stimulation and passive motion which is beneficial for rehabilitating and re-educating muscle function and neurological function. Further, the rehab apparatus disclosed by Wright et al. does not provide prophylactic means for preventing DVT.

U.S. Pat. No. 5,399,147 to Kaiser discloses a CPM orthotic device comprising two carriage members receiving a limb, a hinge interconnecting the two carriage members, a drive means moving the two carriage members reciprocally about the hinge, and a brace. Kaiser further discloses two neuromuscular stimulators integrated with the CPM device, wherein a first stimulator provides muscle stimulation when the limb is fully extended and a second stimulator provides stimulation when the limb is fully contracted. Like the prior rehab apparatus, Kaiser's CPM device does not provide for different sequences of stimulation and passive motion. Moreover, with only two stimulators, NMS benefits only limited areas of the patent's limb.

Some efforts have been made to provide a rehab device combining passive motion with DVT prophylactic therapy. For example, U.S. patent application Publication No. 2011/0077560 to Jacofsky et al. discloses a CPM machine with an integrated mechanical DVT prophylaxis. The CPM machine comprises a base, at least one motor, a plurality of hinged frame rails for imparting passive motion, and a suspension structure for positioning a roller assembly, wherein the roller assembly provides mechanical DVT prophylactic therapy. Jocofsky et al. further discloses a monitoring system to detect blood flow in the limb and provide feedback control to the roller assembly. However, the DVT prophylaxis requires multiple mechanical components in order to achieve suitable prophylactic therapy. In particular, the roller assembly must include multiple rollers, a motor to operate the rollers, a mechanism to adjust the position of the roller assembly to the limb, and a spring to maintain proper pressure against the limb, all of which are necessary for imparting the desired rotational motion needed for prophylactic therapy. With all of its mechanical parts, the CPM machine remains cumbersome, difficult to maneuver and prone to mechanical failure. The CPM machine also lacks other modalities for promoting full range of motion, neurological function, and muscle function in the limb.

While the prior art CPM devices may provide benefits over conventional rehab and postoperative treatment devices, they still suffer from several disadvantages. One of such disadvantages is that the CPM devices do not provide a comprehensive, synergistic treatment of postoperative bodily parts for rehabilitation and re-education of neurological function, muscle function, and range of motion. The prior art CPM devices provide either a single modality or a limited number of modalities for therapeutic treatment. Furthermore, the CPM device and modalities are integrated independently such that the benefits of a coordinated therapy of the CPM and modalities are not achieved. As such, the treatment provided by prior art CPM devices fail to address multiple postoperative complications involved in joint surgeries and may subsequently prolong a patient's time for recovery.

SUMMARY OF THE INVENTION

An object of the present invention is to remedy the problem of needing multiple rehabilitation devices in order to achieve a comprehensive therapeutic treatment for postoperative joints and limbs. The present invention accommodates a patient with a CPM device, or a CPM device and sleeve, for full range of motion support and a plurality of electrodes for transmitting a combination of different modalities. Noted herein, the term "electrodes" encompasses any conductive materials and devices, including electrical coils, electrical plates, electrical conductors, and conductive fabrics and gels. The above configuration of a rehab apparatus produces an improved, synergistic rehabilitation and pain management of postoperative limbs, joints, muscles, and other bodily parts. In particular, the CPM device continuously moves the patient's joint and limb in a reciprocating motion without the patient's muscles being used. While the CPM device is in operation, the electrodes provide a plurality of modalities to the joint and limb to maximize the effectiveness of the therapeutic treatment. The modalities include functional electrical stimulation (FES), transcutaneous electrical nerve stimulation (TENS), temperature therapy, DVT prophylactic therapy, venous blood flow monitoring, and pain monitoring. The FES modality provides electrical impulses to one or more muscle groups in order to induce muscle contractions, which in turn prevents muscle atrophy, increases range of motion, increases blood flow circulation in the limb, reeducates neurological function, decreases spasms, and increases muscle mass. The TENS modality provides pain relief by using electrical current to stimulate nerves near an affected area (e.g. area of injury or area where surgery was performed) and thus mask normal pain. With respect to the temperature therapy modality, heat treatment is used for pain relief and vasodilation to promote muscle relaxation while cold treatment is used for pain relief and vasoconstriction to reduce bleeding in an arterial supply. The DVT prophylactic therapy applies compression and pressure modulation against the limb to aid blood circulation, increase blood flow, and thus prevent the development of DVT. The venous blood flow monitoring is used to detect the occurrence of DVT while the pain monitoring measures the level of pain and controls the delivery of pain medication to the patient.

It is another object of the present invention to provide a rehabilitation apparatus that administers passive, reciprocating motion and a plurality of modalities in a coordinated sequence to the patient's joint and limb. By coordinating the continuous passive motion and application of modalities, the medical benefits of each therapeutic component are combined to form an improved, synergistic treatment regimen.

It is a further object to provide a rehabilitation apparatus that can transmit a plurality of modalities to specific areas of the joint and limb in order to enhance and accelerate rehabilitation.

These and other objectives are achieved by providing a rehabilitation apparatus having a CPM device, a plurality of electrodes, and a control unit, wherein the control unit cooperatively directs the electrodes to transmit a plurality of modalities to a patient's limb and directs the CPM device to provide passive, reciprocating motion in a plane of movement.

These and other objectives are also achieved by providing a non-invasive apparatus for rehabilitating bodily parts immediately in a postoperative period, wherein the apparatus includes a CPM device for passive range of motion therapy, a plurality of electrodes disposed on a patient's limb, and a control unit controlling the electrodes for transmission of at least four modalities chosen from a group consisting of FES, TENS, temperature therapy stimulation, DVT prophylactic stimulation, blood flow monitoring, and pain monitoring. The control unit allows for a coordinated sequence of reciprocating motion and transmission of the at least four modalities to be programmed into the apparatus. In some embodiments, the coordinated sequence is defined by each of the electrodes transmitting one of the at least four modalities simultaneously while the CPM machine is performing a reciprocating motion. In other embodiments, the coordinated sequence is defined by each of the electrodes transmitting one of the at least four modalities simultaneously when the CPM machine is stationary during a pause interval in the reciprocating motion. In yet other embodiments, the controlled sequence is defined by a series transmission of the at least four modalities by all of the electrodes while the CPM machine is moving or during a pause interval. The above embodiments are not exhaustive of all controlled sequences with which the control unit can be programmed.

Other objectives of the invention are achieved by providing a non-invasive apparatus for rehabilitating postoperative body parts, wherein the apparatus includes a CPM device providing passive reciprocating motion to a limb, a plurality of electrodes transmitting a plurality of modalities, and a control unit providing user-dependent control privileges. The capability of providing user-dependent control privileges is accomplished through interactive software programs that are developed for and proprietary to the apparatus and are also capable of interfacing with other third-party medical/therapy software programs. Different user accounts, defined with varying levels of access and control over the apparatus, can be established with the control unit. For instance, a healthcare professional (e.g. doctor, nurse, physical therapist) may have full access to all aspects of the apparatus and full control over programming multiple coordinated sequences of reciprocating motion and transmission of the plurality of modalities. Conversely, a patient may have limited control over the functional aspects of the apparatus. In one case, the patient may only have access to control a subset of the plurality of modalities. In another case, the patient may have control over all modalities but is restricted as to which parameters he or she can manipulate. In yet another case, the patient may have control over a certain parameter of a modality but can only adjust it according to restrictions set by the healthcare professional. In a further case, the patient's control may be limited to only the CPM portion of the apparatus or only the stimulation portion of the apparatus. Thus, the control unit allows a patient to have some input in controlling the rehab apparatus based on user privileges programmed by a healthcare professional responsible for administering the therapeutic treatment and overseeing the function of the apparatus.

Additional objectives of the invention are achieved by providing a non-invasive apparatus for rehabilitating bodily parts that have undergone surgery or that meet other appropriate conditions, wherein said apparatus includes a CPM device for passive range of motion support, a treatment sleeve, a plurality of electrodes disposed on the sleeve, and a control unit controlling the CPM device and the electrodes for transmission of at least four modalities chosen from a group consisting of FES, TENS, temperature therapy stimulation, DVT prophylactic stimulation, blood flow monitoring, and pain monitoring. The CPM device includes one or more attachments adapted to releasably engage the sleeve and thus convey reciprocating motion through the sleeve to the patient's limb. Furthermore, the sleeve and the CPM machine are designed such that each can still be used independently of the other. Thus, the sleeve can be used without being engaged with the CPM device, and the CPM device can be used without removing the sleeve from the limb.

Further objectives are achieved by providing a non-invasive apparatus for rehabilitating postoperative bodily parts, including a CPM device, a sleeve, a plurality of electrodes disposed on the sleeve, a control unit controlling the CPM device to perform reciprocating motion and the electrodes to transmit at least four modalities, and a plurality of conductors electrically connecting the electrodes and CPM device to the control unit. The conductors serve as communication links between the control unit, electrodes, and the CPM device. The control unit is able to send signals representing a coordinated sequence of reciprocating motion and transmission of the at least four modalities to the CPM device and each of the electrodes, respectively.

Additional objectives are achieved by providing a non-invasive device for rehabilitating postoperative bodily parts, including a CPM device, a sleeve, a plurality of electrodes disposed on the sleeve, a control unit controlling the CPM machine to perform reciprocating motion and the plurality of electrodes to transmit at least four modalities, and a plurality of transmitter-receiver units individually disposed within each of the electrodes, CPM device, and control unit. The transmitter-receiver units provide wireless communication between the control unit, CPM device, and electrodes, allowing the control unit to control the CPM device and specific electrodes according to a coordinated sequence of reciprocating motion and transmission of the at least four modalities.

Other objectives of the invention are achieved by providing a non-invasive apparatus for treating a postoperative joint and limb having a CPM device, a sleeve, a plurality of electrodes disposed on the sleeve, wherein each electrode transmits at least four modalities chosen from a group consisting of FES, TENS, temperature therapy stimulation, DVT prophylactic stimulation, blood flow monitoring and pain monitoring, and a control unit electrically connected with a patient-controlled analgesia (PCA) pump. The control unit can administer pain-relief medication via the PCA pump and adjust the dosage according to feedback from the pain monitoring modality.

Further objectives of the invention are achieved by providing a non-invasive apparatus for treating postoperative bodily parts having a CPM device, a sleeve, a plurality of electrodes transmitting a plurality of modalities, and one or more active compression units (e.g. Plexipulse®, sequential compression stockings) connected to one or more of the electrodes transmitting a DVT prophylactic modality for the purposes of applying directional pressure to the limb and preventing DVT.

Further provided is a non-invasive apparatus for joint and limb rehabilitation including a CPM device for range of motion support, a sleeve removably coupled to the CPM device, a plurality of electrodes disposed on the sleeve, and a control unit which controls the CPM device and the electrodes to transmit a plurality of modalities comprising all FES, TENS, temperature therapy stimulation, DVT prophylactic stimulation, blood flow monitoring and pain monitoring.

The rehabilitation apparatus according to the present invention improves therapy and re-education of neurological functions, muscle functions, and range of motion of bodily parts, specifically joints and limbs, that have undergone surgical operations. By applying several different forms of pain management modalities to the joints and limbs, the apparatus increases the efficacy of pain relief and improves therapeutic treatment. Furthermore, with the apparatus conveying a full range of motion and supplying at least four modalities, the present invention avoids the tendency of rejuvenating and re-educating one bodily part while allowing other bodily parts to deteriorate in condition.

The rehab apparatus according to the present invention can also be used in the preoperative setting to optimize the outcome of an upcoming surgery or in the general rehabilitation setting to address common deconditioning and loss of function or range of motion.

Other features and aspects of the invention will become apparent from the following detailed description, taken in conjunction with the accompanying drawings, which illustrate by way of example, the features in accordance with embodiments of the invention. The summary is not intended to limit the scope of the invention, which is defined solely by the claims attached thereto.

DETAILED DESCRIPTION OF THE INVENTION

As used herein, the terms "electrode" and "electrodes" encompass electrical coils, electrical plates, electrical conductors, conductive fabrics and gels, and any other conductive materials and devices.

Figure 1:
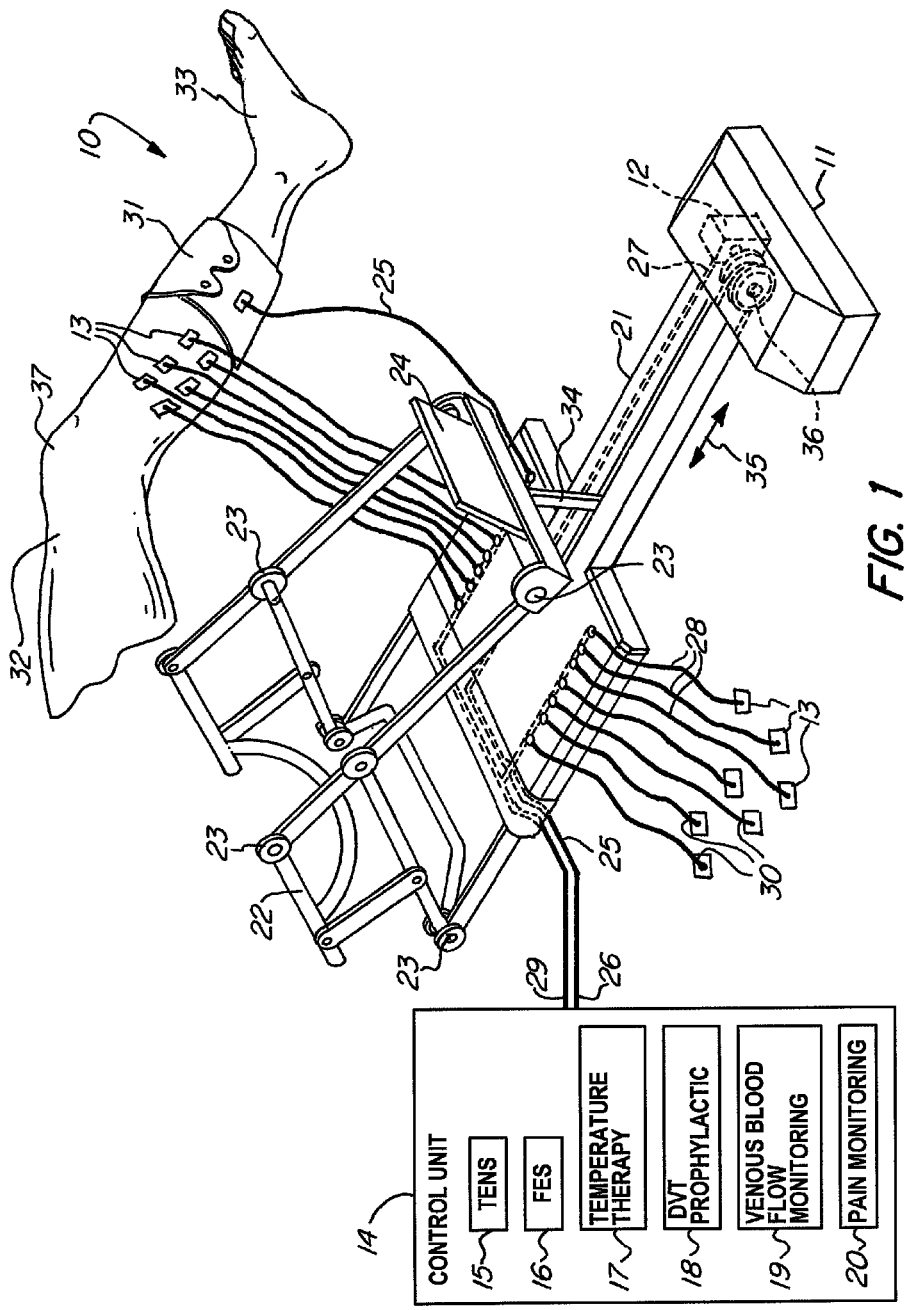
FIG. 1 is a perspective view of a rehabilitation apparatus which provides continuous passive motion and transmits a plurality of modalities according to an exemplary embodiment of the present invention.

Referring to the figures in detail and first to FIG. 1, there is shown an exemplary embodiment of a non-invasive rehabilitation machine with electrodes for providing several modalities to a patient's bodily parts, such as a joint and limb. FIG. 1 illustrates the rehab apparatus 10 with a CPM device 11 and electrodes 13, wherein the CPM device 11 is adapted to receive leg 32 and the electrodes 13 are placed on the leg 32. In order to provide passive motion support, the CPM device 11 has a frame 21, one or more support members 22, and at least one actuator 12, wherein the one or more support members 22 hold and secure the leg 32 to the frame 21. The actuator 12 disposed within the frame 21 is operably connected to the one or more support members 22 at a base 34. As the actuator 12 moves the base 34 in a direction 35, the one or more support members 22 pivot along one or more hinges 23. This configuration creates a reciprocating motion, wherein the reciprocating motion involves the actuator 12 continuously and cyclically disposing the one or more support members 22 in an extension position and a flexion position. When the CPM device 11 is in the extension position, the base 34 is disposed proximate to the actuator 12, whereas the base 34 is disposed away from the actuator 12 when the CPM device 11 is in the flexion position. When the support members 22 move back and forth between the extension position and the flexion position, a knee 37 stretches and bends, respectively. Thus, a passive, full range of motion is imparted to the leg 32.

Figure 7:
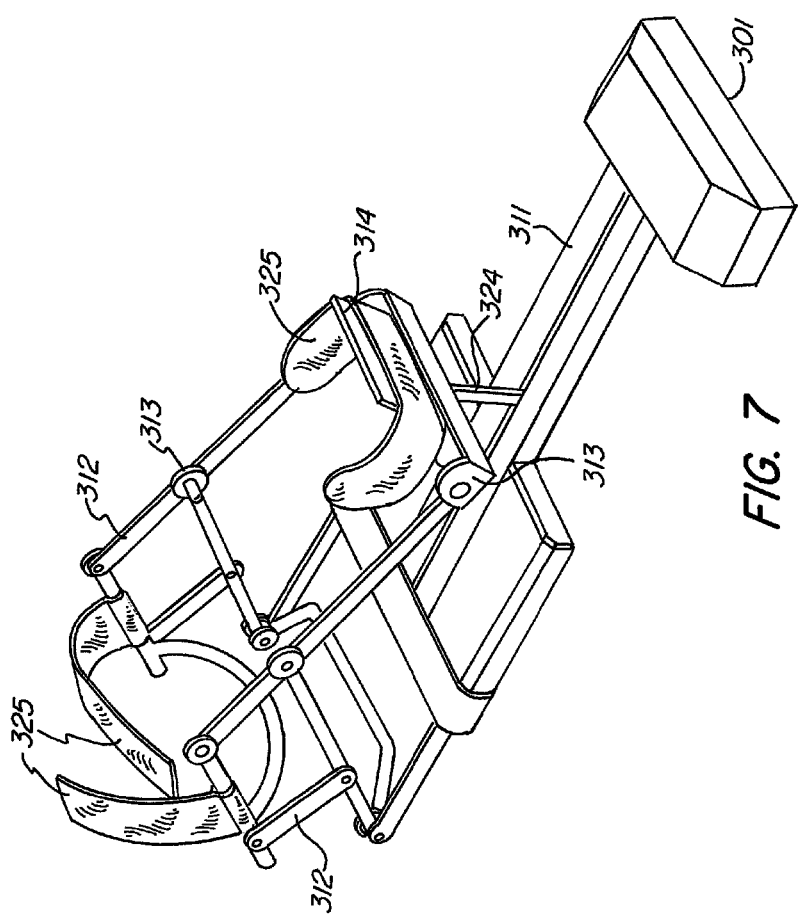
FIG. 7 is a perspective view of the rehabilitation apparatus shown in FIG. 6 with attachments for releasably engaging a CPM device with a treatment sleeve.

A foot rest 24 adapted for receiving a foot 33 and a plurality of attachments (see 325 in FIG. 7) disposed along the one or more support members 22 and the foot rest 24 help to secure the leg 32 to the CPM device 11. This prevents any slipping and separation between the one of more support members 22 and leg 32 and between the foot rest 24 and foot 33. The attachments provide passive motion support to the leg 32 when the CPM device 11 moves into either the extension or flexion position. The foot rest 24, which is fixed to the base 34, provides additional passive motion support to the leg 32 when the CPM device 11 approaches the flexion position. Any material providing for secure engagement can be used to make the attachments. For example, they can comprise VEL-CRO® straps with hook and loop surfaces to secure the leg 32 to the one or more support members 22. Other materials and methods, however, can also be used to make the attachments.

The plurality of electrodes 13 removably attach to the leg 32 anywhere and in any configuration (e.g. parallel, series, staggered, etc.), including an upper portion (i.e. thigh) and lower portion (i.e. calf and foot) of the leg 32. As illustrated in FIG. 1, the electrodes 13 are positioned on the side of the calf of leg 32 in a series-parallel configuration. Alternatively, the electrodes 13 can be positioned on an anterior or posterior of the leg 32. However, in order to maximize the therapeutic benefits of the modalities, the electrodes 13 can be positioned on or closely around specific parts of the leg 32 that require concentrated therapy and pain relief compared to other parts of the leg 32.

The rehab apparatus 10 also includes one or more conductors that electrically connect the actuator 12 and electrodes 13 with the control unit 14. In particular, the one or more conductors can comprise a first conductor 25 having a proximal end 26 connected to the control unit 14 and a distal end 27 connected to the actuator 12. Accordingly, the first conductor 25 provides communication between the control unit 14 and the actuator 12 in order to control the reciprocating motion of the CPM device 11. Further, the rehab device 10 comprises at least one second conductor 28 having a proximal end 29 connected to the control unit 14 and a distal end 30 connected to one or more electrodes 13. In one embodiment, the control unit 14 controls the electrodes 13 to transmit a plurality of modalities, wherein the modalities comprise at least four modalities chosen from a group consisting of FES 16, TENS 15, temperature therapy stimulation 17, DVT prophylactic stimulation 18, venous blood flow monitoring 19, and pain monitoring 20. In another embodiment, the control unit 14 directs the electrodes 13 to transmit modalities comprising any five of the above specified modalities. In yet another embodiment, the control unit 14, directs the electrodes 13 to transmit modalities comprising all six FES 16, TENS 15, temperature therapy stimulation 17, DVT prophylactic stimulation 18, venous blood flow monitoring 19, and pain monitoring 20.

The control unit 14 further establishes a coordinated sequence of reciprocating motion of the CPM device 11 and transmission of the plurality of modalities by the electrodes 13. In one embodiment, the coordinated sequence of transmission is defined by a first group of electrodes transmitting a first modality of the plurality of modalities, a second group of electrodes transmitting a second modality of the plurality of modalities, a third group of electrodes transmitting a third modality, and a fourth group of electrodes transmitting a fourth modality, wherein the first, second, third, and fourth groups simultaneously transmit the first, second, third, and fourth modalities, respectively. During this type of operation of the rehab apparatus 10, the simultaneous transmission of modalities occurs when the one or more support members 22 are in reciprocating motion. In a second embodiment, the coordinated sequence of transmission is defined by the electrodes 13 simultaneously transmitting the same modalities while the one or more support members are in reciprocating motion. In a third embodiment, the coordinated sequence is defined by the electrodes 13 transmitting in series one of the modalities. In still another embodiment, the coordinated sequence of transmission can be defined by the serial transmission of each of the modalities by all electrodes 13. Additional coordinated sequences can be established by implementing the previously described transmissions during a pause interval in the reciprocating motion when the one or more support members 22 are stationary. Note, the above examples are representative but not exhaustive of the coordinated sequences performed by the rehab device 10 embodying the present invention. The control unit 14 allows for more than one coordinated sequence to be programmed and stored into memory for use in later treatment sessions with the rehab device 10.

In order to determine what position the support members 22 are in (e.g. extension position, flexion position, or an intermediate position), the CPM device 11 comprises a position sensor 36 disposed at the actuator 12. Other position sensors can also be placed on the support members 22, hinges 23, or base 34 to further ascertain the status and condition of the CPM device 11. The position information that is obtained by the sensor 36 is communicated to the control unit 14 via first conductor 25 and then used to make any necessary adjustments to the CPM device 11 to achieve the appropriate reciprocating motion.

Figure 2A:
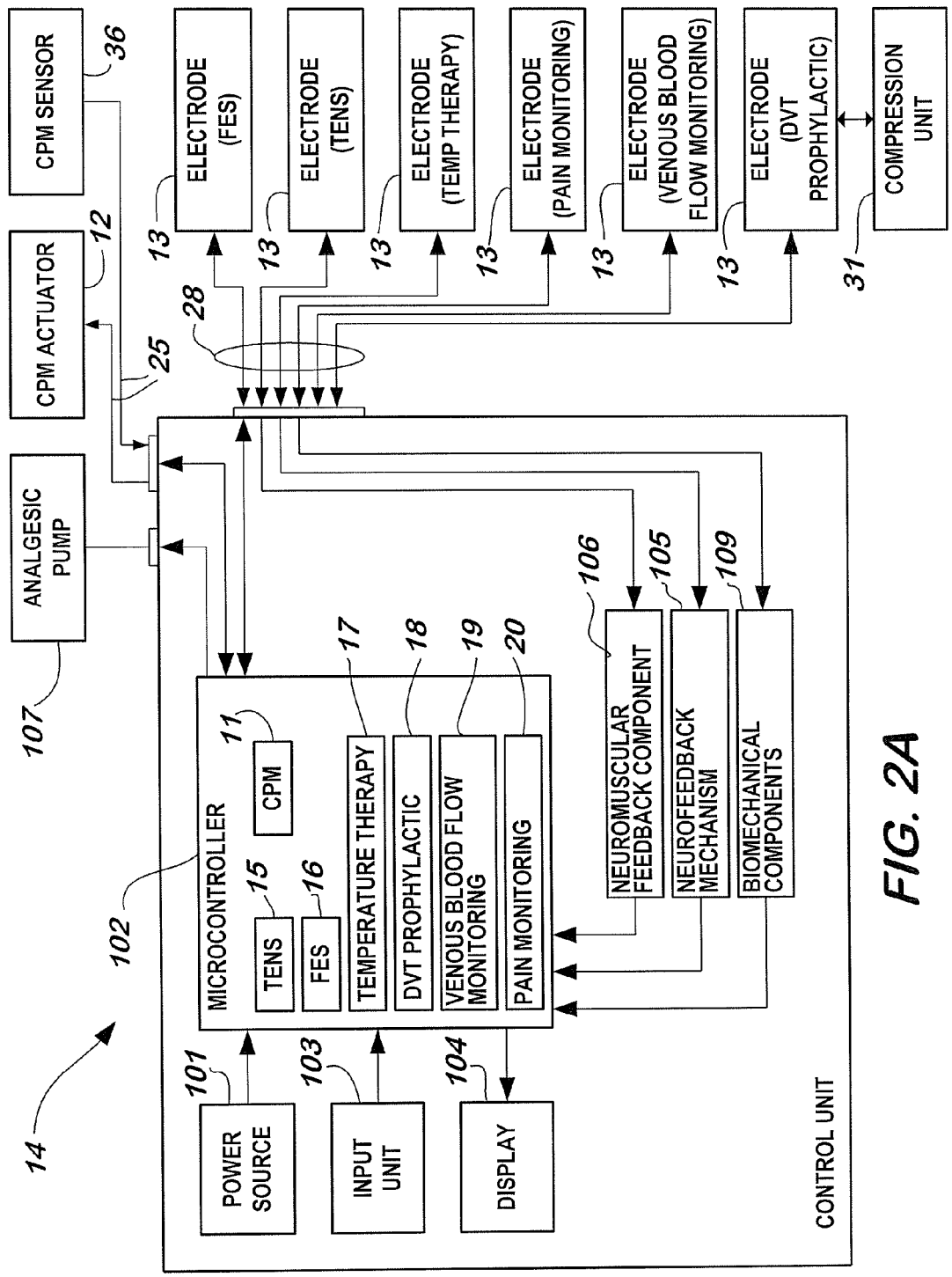
FIGS. 2A and 2B are block diagrams illustrating a control unit in communication with a CPM device and a plurality of electrodes for controlling reciprocating motion and transmission of a plurality of modalities, according to an exemplary embodiment of the present invention.
Figure 2B:
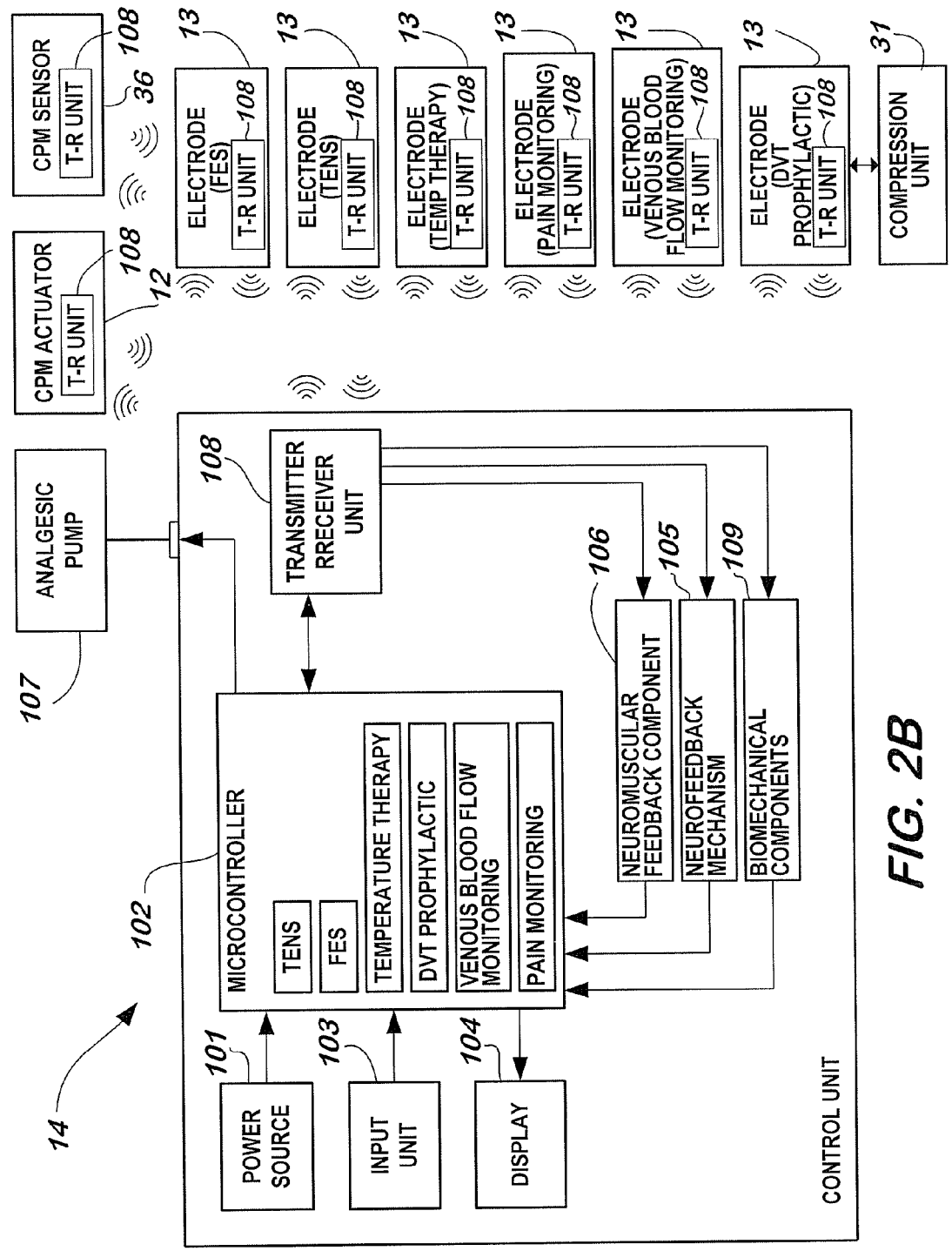

FIGS. 2A and 2B show block diagrams of two embodiments of the control unit. As shown in FIG. 2A, the control unit comprises a power source 101 for supplying energy to the control unit 14, a microcontroller 102 for controlling the CPM device 11 and the electrodes 13 according to the coordinated sequence of reciprocating motion and transmission of the at least four modalities (chosen from the group consisting FES 16, TENS 15, temperature therapy stimulation 17, DVT prophylactic stimulation 18, venous blood flow monitoring 19, and pain monitoring 20), an input unit 103 for manipulating and programming the coordinated sequence into the microcontroller 102, and a monitor 104 for displaying a status of the CPM device 11, a status of each of the electrodes 13 and the coordinated sequence. In one embodiment, the power source 101 comprises an energy cell or portable battery pack. In another embodiment, energy is supplied to the control unit 14 through an electrical cord (not shown) having one end connected to the control unit 14 and another end connected to an electrical socket. With regards to the input unit 103, one embodiment of this element comprises an alpha-numeric keypad or keyboard (see FIG. 3). In an alternative embodiment, the input unit 103 is combined with the monitor 104 to provide a touch screen interface responsive to a touch by the user (e.g. patient undergoing treatment session with the rehab device, healthcare professional administering treatment session).

In one embodiment, the control unit 14 includes a neuromuscular feedback component 106 electrically connected to the microcontroller 102 and electrodes 13 via second conductors 28. The neuromuscular feedback component 106 functions to observe and record a response in a muscle mass upon the transmission of a FES modality 16. Using the recorded muscle response and information on the coordinated sequence, the neuromuscular feedback component 106 adjusts the FES modality 16. Specifically, the neuromuscular feedback component 106 can change the magnitude, duration, or other parameter of the FES modality 16. The neuromuscular feedback component 106 may also modify the controlled sequence of transmission by changing the modality from FES 16 to TENS 15, temperature therapy stimulation 17, DVT prophylactic stimulation 18, venous blood flow monitoring 19, or pain monitoring 20. In another embodiment, the stimulation control unit 14 includes a neurofeedback mechanism 105 connected to the microcontroller 102 and the electrodes 13 via second conductors 28. Similar in the configuration of the neuromuscular feedback component 106, the neurofeedback mechanism 105 observes and records a response in a nerve or group of nerves upon the transmission of the TENS modality 15. The neurofeedback mechanism 105 then adjusts the TENS modality 15 according to the nerve response. As an example, the neurofeedback mechanism 105 can tune the magnitude or duration of the TENS modality 15 or modify the controlled sequence of transmission by changing the modality from TENS 15 to FES 16, temperature therapy stimulation 17, DVT prophylactic stimulation 18, venous blood flow monitoring 19, and pain monitoring 20. In another embodiment, the control unit 102 includes both the neuromuscular feedback component 106 and the neurofeedback mechanism 105 to adjust the controlled sequence of reciprocating motion and transmission of modalities based on recorded responses in the muscles and nerves.

According to another embodiment of the present invention, the control unit 14 has a biomechanical component 109 connected to the electrodes 13 via the second conductors 28. Using the electrodes 13, the biomechanical component 109 monitors and analyzes biomechanical responses and range of motion of the limb and joint throughout the operation of the rehab apparatus 10. The control unit 14 can therefore gauge the progression of the patient's rehabilitation and adjust the coordinated sequence of reciprocating motion and transmission of modalities to ensure optimum therapeutic treatment. Based on the biomechanical responses and range of motion data, the biomechanical component 109 can adjust one or more of the at least four modalities. For example, the biomechanical component 109 can change the magnitude and/or duration of the FES modality 16, TENS modality 15, or both FES 16 and TENS 15. As another example, the biomechanical component can adjust the temperature therapy stimulation 26 by either increasing or decreasing the temperature applied to the patient's leg to promote healing in the limb, joint, muscles, and other bodily parts. Specifically, pain relief and vasodilation for muscle relaxation can be accomplished by transmitting warm-to-hot temperatures to the limb and joint while transmitting cool-to-cold temperatures reduces inflammation and decreases pain and spasms. The biomechanical component 109 can also change the type of modality being transmitted. With respect to the reciprocating motion, the biomechanical component 109 can modify various parameters (e.g. speed, duration, range, and technique) of the CPM device 11 in order to obtain a desirable form of passive reciprocating motion. In view of the above, the combination of the neuromuscular feedback component 106, neurofeedback mechanism 105, and the biomechanical component 109 creates feedback control over the transmission of modalities and generation of reciprocating motion.

FIG. 2A also show a compression unit 31 electrically connected to an electrode 13 providing the DVT prophylactic modality 18. Upon receiving a signal for DVT prophylactic modality 18, the compression unit 31 applies directional and/or non-directional pressure to the leg 32 in order to increase blood circulation and simulate the movement of blood produced during walking. In one embodiment, the compression unit 31 is a sequential compression device comprising an inflatable compression sleeve that is adapted to wrap around the leg 32 and/or foot 33. In another embodiment, the compression unit 31 comprises a Plexipulse®-type device. Because of the connection between the electrodes 13 and control unit 14, the compression unit 31 is also configurable by the user. Specifically, the user can define the frequency, intensity and duration of the inflation and deflation of the compression unit 31. Furthermore, the control unit 14 can dynamically adjust the frequency, intensity and duration of the compression unit 31 according to the coordinated sequence of reciprocating motion and transmission of the plurality of modalities.

A patient-controlled analgesia (PCA) pump 107 is also in connection with the control unit 14. When the pain monitoring modality 20 is transmitted to one or more of the plurality of electrodes 13, a pain level is measured in the patient's leg 32. This information is subsequently communicated back to the control unit 14 through the one or more second conductors 28. Upon analyzing the pain level information in view of the coordinated sequence of reciprocating motion and transmission, the control unit 14 directs the PCA pump 107 to administer a certain dosage of pain medication. In addition, the control unit 14 can utilize the pain information provided by the pain monitoring modality 20 to adjust other pain relief modalities (i.e. TENS 15 and temperature therapy 17). As a result, regardless of the intensity of treatment provided by the rehab apparatus 10, the amount of pain that the patient feels can be kept to a minimum.

As shown in FIG. 2B, a second embodiment of the control unit 14 comprises a power source 101, a microcontroller 102, an input unit 103, a monitor 104, and a transmitter receiver unit 108. Moreover, each of the electrodes 13, actuator 12, and sensor 36 comprises a transmitter-receiver unit 108, allowing for the control unit 14 to wirelessly send the coordinated sequence to these components as well as receive feedback from these components. The transmitter-receiver units 108 also communicate recorded muscle responses, nerve activity, and biomechanical responses detected by the electrodes 13 to the neuromuscular feedback component 106, neurofeedback mechanism 105, and biomechanical component 109, respectively. Likewise, blood flow measurements from the one or more electrodes 13 transmitting the venous blood flow monitoring modality 19 and pain level measurements from the one or more electrodes 13 transmitting the pain monitoring modality 20 are sent back wirelessly to the microcontroller 102. With multiple feedback loops created between the electrodes 13, actuator 12, and microcontroller 102, the control unit 14 can automatically and dynamically adjust the coordinated sequence of reciprocating motion and transmission of the plurality of modalities to achieve an improved therapeutic treatment.

As it appears in FIG. 2B, the analgesia pump 107 is in wired communication with the microcontroller 102. However, similar to the electrodes 13, the analgesia pump 107 can include its own transmitter-receiver unit 108 and thus eliminate any need for a physical connection (i.e. conductor). As such, the rehab device 10 can be completely wireless and require no physical connection between the CPM device 11, electrodes 13, and control unit 14.

Figure 3:
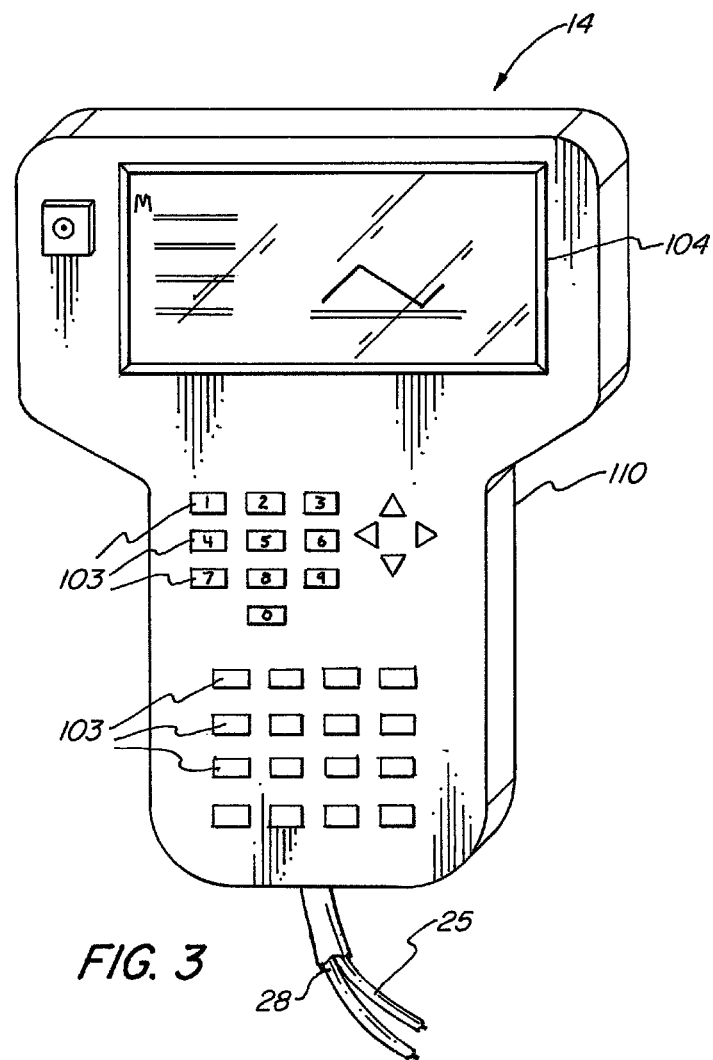
FIG. 3 is a front view of a control unit for controlling the reciprocating motion of a CPM device and the transmission of a plurality of modalities by electrodes according to an exemplary embodiment of the present invention.

FIG. 3 is a front view of the control unit 14 as embodied in FIG. 2A. Using the input unit 103, the user can program a coordinated sequence of reciprocating motion and transmission of modalities into the microcontroller 102 while viewing a system interface displayed on the monitor 104. For example, a healthcare professional can design one or more coordinated sequences through the control unit 14—based on the patient's medical condition—by defining all the parameters associated with producing a particular reciprocating motion and transmission of modalities. The healthcare professional can then save the coordinated sequences and select any one of them for use in future treatment sessions. When a coordinated sequence is selected, the microcontroller 102 sends signals to the actuator 12 via first conductor 25 and to each of the electrodes 13 via second conductors 28 to produce the appropriate passive motion and modality transmission.

Where a patient is the user, the patient can use the control unit 14 to adjust certain parameters of the coordinated sequence and thus tailor it according to his or her medical condition. For example, the patient can set the actuator 12 of the CPM device 11 to provide a uniform speed for the cycles of reciprocating motion. Alternatively, the speed can be set such that it gradually increases or decreases with time. The control unit 14 further allows for the speed of the CPM device 11 to vary during a cycle or between successive cycles of the reciprocating motion. In another instance, the patient can adjust the technique of the reciprocating motion. Specifically, the reciprocating motion can be programmed to have a consistent range of motion (i.e. the amount that the knee 37 bends and stretches stays the same) throughout an entire treatment session of the rehab device 10. In cases where the patient has undergone extensive surgery on the knee 37, the reciprocating motion can start with a limited range of motion and gradually increase to a full range of motion of the leg 32. Just like the reciprocating motion aspect of the coordinated sequence, the patient can customize the parameters related to the modality transmission.

The control unit 14 also has the capability of restricting control over the operation of the rehab apparatus 10 based on whether the user is a patient or a healthcare professional. Control can further be limited according to whether the healthcare professional is a doctor, nurse, physical therapist, or other medical practitioner. The control unit 14 provides these different control privileges through interactive software programs developed to control and function with the rehab apparatus 10. Such interactive software programs are also capable of interfacing with other third-party software applications having medical/therapy-related functions, such as medical diagnosis, medical analysis, and data collection and management. Thus, the control unit 14 resembles a typical computer operating system with different user accounts (e.g. administrator account having capability to make system-wide changes, personal user accounts having capability to change select settings, guest accounts having little to no authority in making any changes). As an "administrator," the healthcare professional can program a coordinated sequence of reciprocating motion and transmission of modalities, set all parameters associated with each modality and the reciprocating motion, and establish what privileges another user, such as the patient, can have in adjusting the operation of the rehab apparatus. The patient can have the same level of control over the rehab apparatus 10 as the healthcare professional. On the other hand, the patient may have limited control, wherein the patient can tailor certain modalities and/or the reciprocating motion to his individual medical situation as long as it is within any restrictions and parameters programmed into the control unit by the treating or supervising healthcare professional. The healthcare professional may configure the control unit such that the patient cannot design a coordinated sequence of treatment or is prohibited from making certain changes to the coordinated sequence created by the healthcare professional. In one instance, the patient may only have the ability to adjust a subset of the plurality of modalities. For example, where the transmission of modalities comprises FES 16, TENS 15, DVT prophylactic stimulation 18, and venous blood flow monitoring 19, the patient may merely have control over the venous blood flow monitoring 19. The patient may also experience restrictions on the extent that any one of the modalities can be adjusted. In particular, only certain parameters of a given modality may be modified by the patient. For example, the patient may be able to modify the duration of the FES modality 16 but not the intensity. Still further, the healthcare professional may allow the patient to adjust a parameter of a given modality, but only within a set range defined by a minimum and maximum. In one example, the patient is permitted to adjust the temperature settings of the temperature therapy stimulation 17, but only within a 60-100° F. range. In another example, the patient can control delivery of pain medication by the PCA pump associated with the pain monitoring modality 20 but only within the frequency and dosage restrictions set by the healthcare professional. This feature of the control unit 14, wherein a level of control can be set according to the type of user (e.g. healthcare professional or patient), is advantageous because it safeguards against the patient inadvertently adjusting the coordinated sequence of reciprocating motion and modality transmission to a less-than-optimal form of treatment.

In one embodiment, the control unit 14 comprises a unit fastener (not shown) disposed on a side 110. The unit fastener allows for the control unit 14 with conductors 25, 28 to be releasably attached to the CPM device 11. In another embodiment, the control unit 14 having a transmitter-receiver unit can be a standalone unit. This particular configuration of the control unit 14 allows it to be mobile and free of any physical connection to the electrodes 13 and CPM device 11. As a result, a healthcare professional can continuously supervise the progress of a patient undergoing a treatment session with the rehab apparatus without being in the same room as the patient.

Figure 4A:
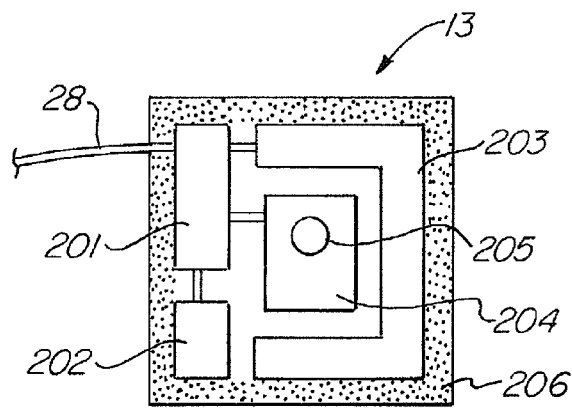
FIGS. 4A and 4B are top views of a stimulating electrode in wired communication and wireless communication with a control unit, respectively.
Figure 4B:
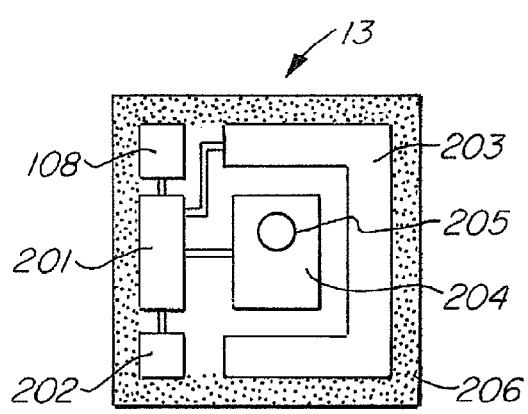

FIG. 4A and 4B are top views of two embodiments of the electrode 13. In FIG. 4A, the electrode 13 comprises a signal generator 201 connected to second conductor 28, and a temperature unit 202 and transmission layer 203 in direct contact with the patient's leg 32. Conversely, the electrode 13 can comprise a transmitter-receiver unit 108 and need not require connection to a conductor, as shown in FIG. 4B. Signal generator 201 receives and interprets the coordinated sequence of transmission from the control unit 14 and supplies an electrical current to temperature unit 202 or transmission layer 203 for providing one of the modalities. If the electrode 13 is directed to transmit either FES 16, TENS, 15, or DVT prophylactic modality 18, the signal generator 201 supplies the electrical current to the transmission layer 203 which in turn executes the required stimulation to the leg 32. With respect to the DVT prophylactic modality 18, the electrode 13 is connected to the compression unit 31 (see FIG. 1). Details regarding the electrical connection between the compression unit and the electrode are discussed further below. The transmission layer 203 also serves to monitor a response or activity of a bodily part (e.g. muscle response, nerve activity, biomechanical response) and communicates such information back to the microcontroller 102, neuromuscular feedback component 106, neurofeedback mechanism 105, and biomechanical component 109.

In the case where the electrode 13 is directed to transmit temperature therapy stimulation 17, the signal generator 201 supplies electrical current to the temperature unit 202. The temperature unit 202 in turn provides either heating or cooling to the leg 32. The cooling provides pain relief and causes vasoconstriction of arterial supply to help reduce any bleeding immediately following surgery on the leg 32. The heating helps with relieving pain associated with movement of the patient's leg 32 and causes vasodilation for muscle relaxation. In one embodiment, the temperature unit comprises electrical coils to produce the appropriate temperature for the heating or cooling effect of the temperature therapy stimulation.

In another case where the electrode 13 is directed to provide venous blood flow monitoring 19 or pain monitoring 20, the signal generator 201 supplies electrical current to the transmission layer 203 which further comprises a detection layer 204. For the pain monitoring modality 20, the detection layer 204 is capable of detecting and measuring the level of pain the patient experiences during a therapy session with the rehab device 10. The pain level information is then sent back to the control unit 14 and used to administer the appropriate amount of pain medication via the analgesia pump 107. Furthermore, the pain level information can be used by the microcontroller 102 to dynamically adjust the coordinated sequence of reciprocating motion and transmission of the plurality of modalities. With regards to the venous blood flow monitoring modality 19, the detection layer 204 further comprises a non-invasive ultrasound Doppler 205 for examining blood flow and determining whether DVT is developing. The blood flow information is subsequently sent back to the control unit 14 for additional analysis by the microcontroller 102, which in turn properly adjusts the coordinated sequence.

Figure 5:
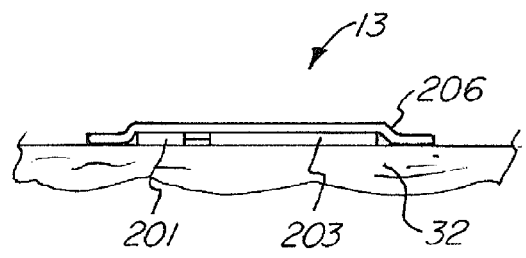
FIG. 5 is a side elevation view of the electrode shown in FIG. 4A.

To maintain direct contact between the leg 32 and the temperature unit 202, transmission layer 203, and detection layer 204, the electrode 13 has a fastening layer 206 for providing removable attachment to a skin of the leg 32. In one embodiment, the fastening layer 206 comprises an adhesive component, often seen in adhesive bandages. When the electrode 13 is placed on the leg 32, a center portion of the fastening layer 206 covers the signal generator 201, temperature unit 202, transmission layer 203, and the detection layer 204 while a peripheral portion of the fastening layer 206 directly adheres to the leg 32 (see FIG. 5). In another embodiment, the fastening layer 206 comprises a VELCRO® strap which wraps around the leg 32 and secures the electrode 13 against the skin. The fastening layer 206 can comprise other means known in the art for removably attaching items to a bodily part and is not limited to the above two embodiments.

Figure 6:
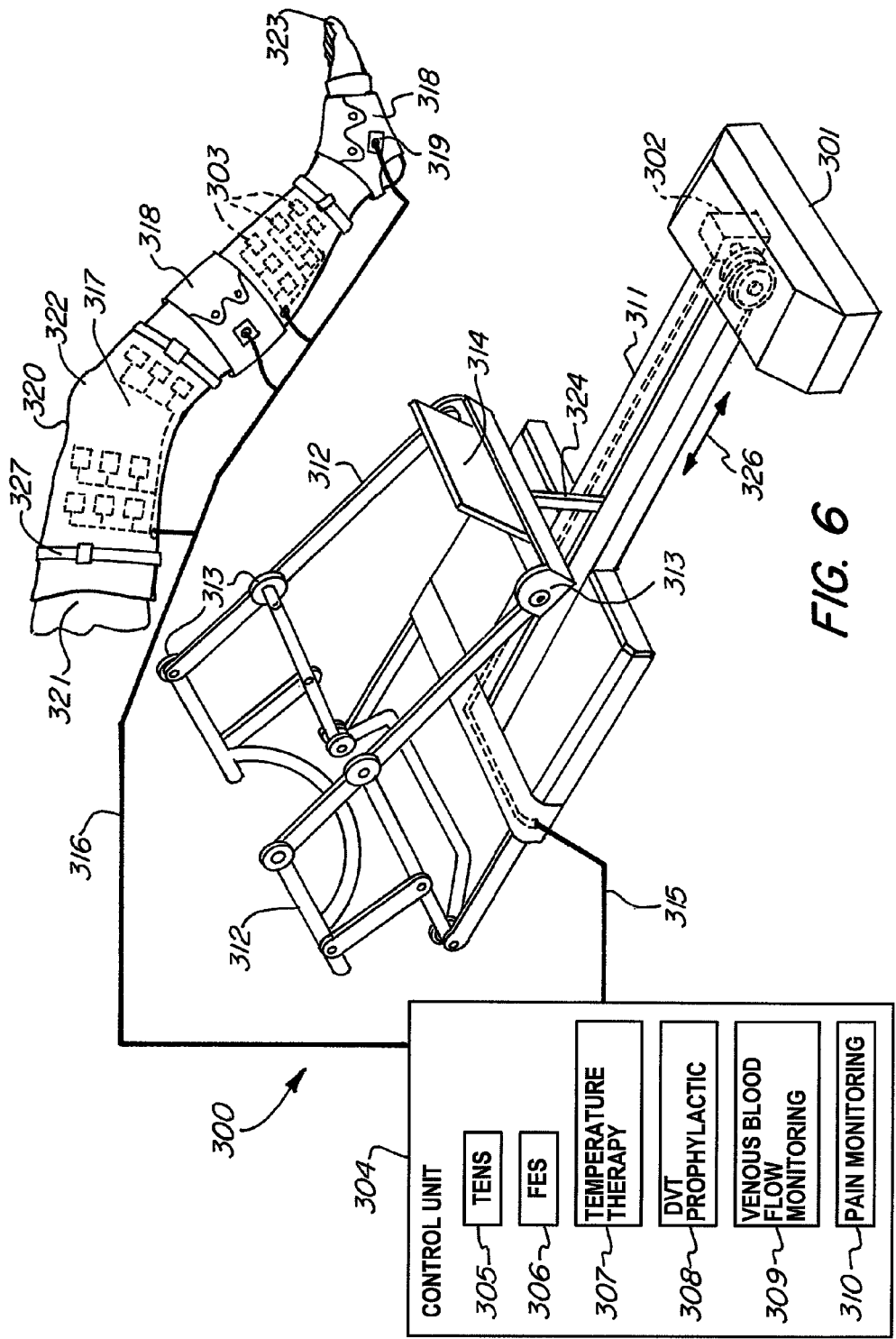
FIG. 6 is a perspective view of a rehabilitation apparatus providing continuous passive motion and transmitting a plurality of modalities according to a second embodiment of the present invention.

Referring to FIG. 6, there is shown a second embodiment of the rehabilitation apparatus according to the present invention. FIG. 6 shows a non-invasive, rehab apparatus 300 having a CPM device 301, a sleeve 317, a plurality of electrodes 303 disposed on the sleeve 317, a plurality of conductors 315, 316 each having a proximal end connected to a control unit 304 and a distal end connected to either the CPM device 301 (i.e. actuator 302) or one or more electrodes 303. The CPM device 301 comprises a frame 311, support members 312 providing passive motion support to a leg 320, foot rest 314, hinges 313, and at least one actuator 302. The actuator 302 disposed within the frame 311 is operably connected to the support members 312 at a base 324. As the actuator 302 operates to move the base 324 in a direction 326, the support members 312 pivot along the hinges 313, creating a reciprocating motion characteristic of the CPM device 301. One or more attachments 325 (see FIG. 7) disposed along the support members 312 and at foot rest 314 help to releasably secure the sleeve 317 to the CPM device 301 and prevent any slipping between the support members 312 and the sleeve 317. Further, the attachments 325 provide additional passive motion support to the sleeve 317, and in turn leg 320, while the CPM device 301 is moving back and forth between the extension position (i.e. knee 322 stretches) and the flexion position (i.e. knee 322 bends). Despite this releasable engagement, the CPM device 301 and sleeve 317 remain independent components such that they can function without the other. More specifically, the sleeve can still be used without being engaged with the CPM device and the CPM device can be used with or without removing the sleeve 317 from the leg.

Figure 8A:
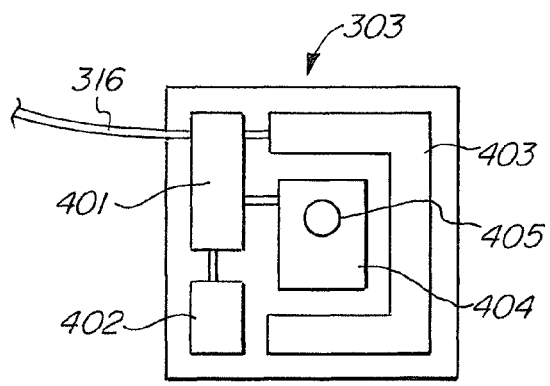
FIGS. 8A and 8B are top views of a second embodiment of the stimulating electrode in wired communication and wireless communication with a control unit, respectively.
Figure 8B:
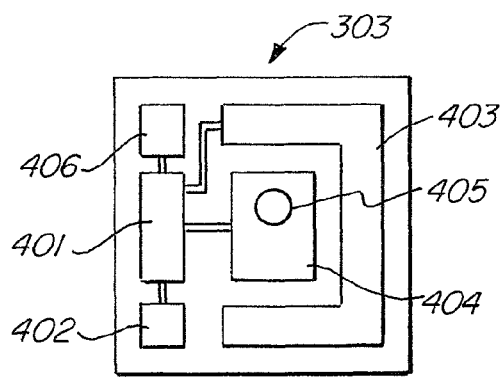

The sleeve 317 is made of a material having elastic properties and has a tubular shape adapted to fit over and conform to the patient's entire leg 320, from a thigh 321 down to a foot 323. The sleeve 317 maintains constant contact with the leg 320 and knee 322 while allowing flexibility for full range of motion. To further ensure that the sleeve 317 is secured and closed around the leg 320, one or more sleeve fasteners 327 disposed on an outer lining of the sleeve 317 are provided. The plurality of electrodes 303 are disposed on the sleeve 317, being removably attached to an inner lining to provide for transcutaneous transmission of the at least four modalities to the leg 320. As illustrated in FIGS. 8A and 8B, the electrodes 303 each have a signal generator 401 interpreting the coordinated sequence of transmission from the control unit 304 and supplying electrical current to a temperature unit 402, a transmission layer 403, a detection layer 404, and an ultrasound Doppler 405. The temperature unit 402 is adapted to provide a temperature therapy stimulation 307, while the transmission layer 403 is adapted to provide TENS 305, FES 306, and DVT prophylactic modality 308. In order to provide a pain monitoring modality 310 and venous blood flow monitoring modality 309, the electrode 303 uses the detection layer 404 and ultrasound Doppler 405, respectively. FIG. 8A, in particular, shows a top view of one embodiment of the electrode 303 having the conductor 316 electrically connected to the signal generator 401 for wired communication with the control unit 304. Alternatively, the electrode 303 can be in wireless communication with the control unit 304 when both the electrode 303 and the control unit 304 have transmitter-receiver units 406, as shown in FIG. 8B.

Figure 9:
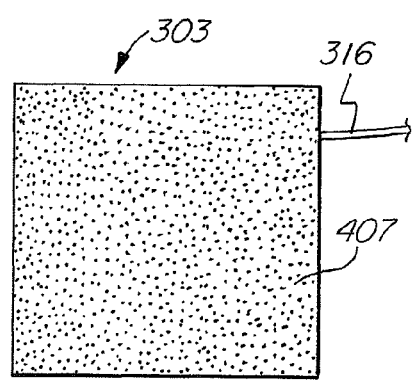
FIG. 9 is bottom view of the electrode shown in FIG. 8A.
Figure 10:
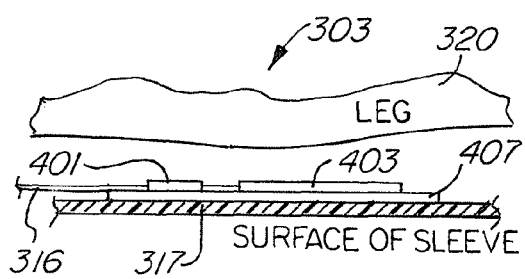
FIG. 10 is a side elevation view of the electrode shown in FIG. 8A.

FIG. 9 shows a bottom view of the electrode 303 having fastening layer 407. The fastening layer 407 provides a means for the electrode 303 to removably attach to the inner lining of the sleeve 317 without interfering with the direct contact between the leg 320 and the temperature unit 402, transmission layer 403, and detection layer 404 (see FIG. 10). In one embodiment, the fastening layer 407 can be made of VELCRO® to achieve a secure attachment to the inner lining of the sleeve 317. The fastening layer 407 allows for easy repositioning of the electrodes 303 on the sleeve in order to accommodate the patient's unique anatomy or to concentrate the transmission of modalities to certain areas of the patient's leg 320. Furthermore, the electrode 303 with signal generator 401, temperature unit 402, transmission layer 403, detection layer 404, and ultrasound Doppler 405 still maintains a small foot print. Therefore, the electrode 303 lies substantially flush with the inner lining of the sleeve 317 once the patient wears the sleeve 317 on his leg 320.

Figure 11:
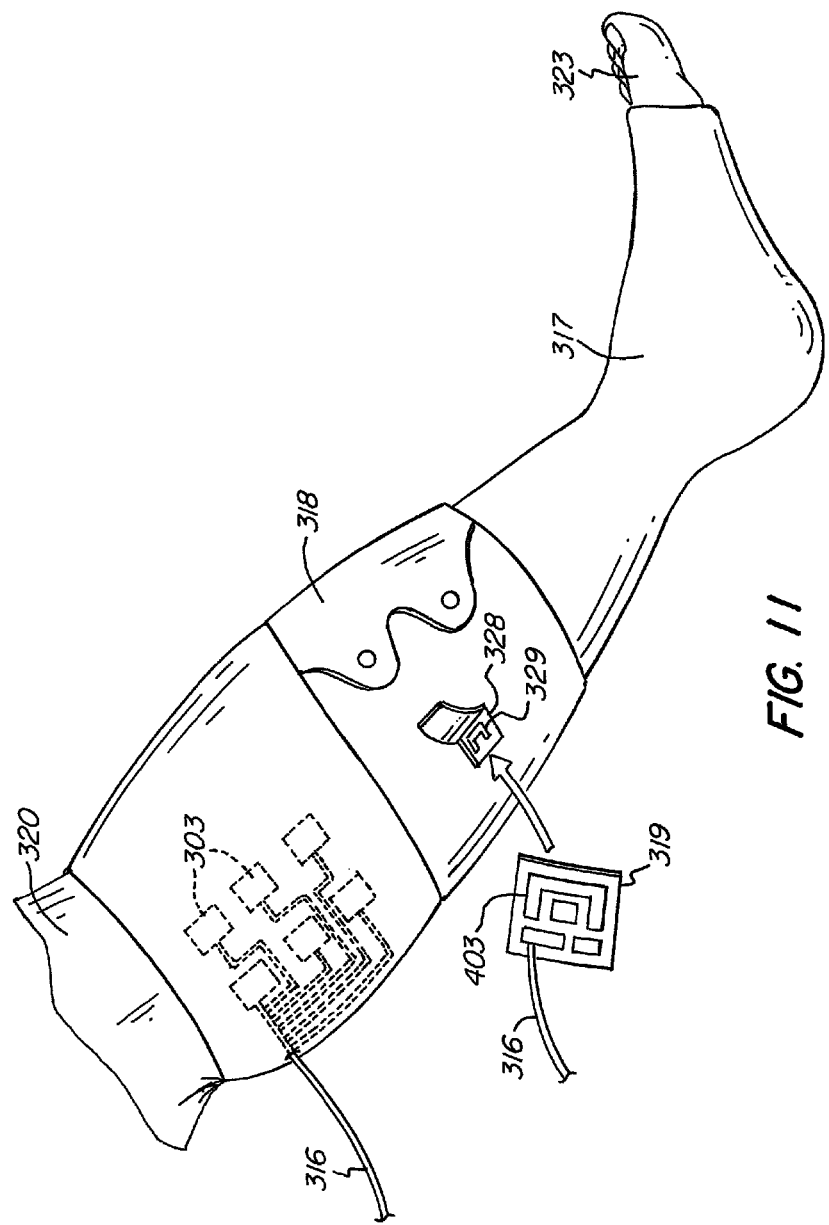
FIG. 11 is detailed view of the sleeve of the rehabilitation apparatus shown in FIG. 7 with electrodes disposed on the sleeve and one of the electrodes removably coupled to a compression unit.

Referring to FIG. 11, there is shown an embodiment of the sleeve 317 of the rehab device 300 according to the present invention. FIG. 11, in particular, demonstrates a sleeve 317 having a plurality of electrodes 303 disposed on its inner lining. Further, a compression unit 318 for providing the DVT prophylactic modality 308 is disposed on the sleeve 317. The compression unit 318 comprises an insert slot 328 adapted to receive an electrode 319 transmitting the DVT prophylactic modality 308. The electrode 319 has the same characteristics and components as the electrodes 303. Upon inserting the electrode 319 into the insert slot 328, the transmission layer 403 comes in direct contact with a corresponding receiving layer 329 disposed within the slot 328. An electrical connection is subsequently created between the transmission layer 403 and the receiving layer 329, which allows for the compression unit 318 to receive control signals from the control unit 304. In one embodiment, the compression unit 318 is a separate unit having means for removably attaching it to the sleeve 317. In a second embodiment, the compression unit 318 can form a part of the sleeve 317, whereby the compression unit 318 is directly sewn into the sleeve 317. As such, the sleeve 317 forms a single complete unit with electrodes 303 (and electrode 319) and the compression unit 318, thus allowing for quick and easy placement on and removal from the patient's leg 320.

Although the invention has been described with reference to particular arrangement of parts, features, and the like, these are not intended to exhaust all possible arrangements or features, and indeed many modifications and variations will be ascertainable to those of skill in the art. The present invention is designed so that any electrical or mechanical treatment modalities that are available but have not been incorporated into the description of the invention, or that become available as technology advances, are considered part of the invention and incorporated by modifying the electrical and mechanical parts and protocols associated with them to the extent that such additional electrical or mechanical advances encompass any combination of the above described four or more treatment modalities.

What is claimed is:

1. A non-invasive apparatus for rehabilitating a joint, limb, and muscles of a patient recovering from surgery on the joint, the apparatus comprising:
   a continuous passive motion (CPM) device having a frame, at least one support member for supporting and securing the limb to the frame, at least one hinge coupled to the at least one support member, and at least one actuator for providing reciprocating motion of the at least one support member about the at least one hinge;
   a plurality of electrodes configured to be disposed on the limb, wherein the plurality of electrodes transmit at least the following four modalities: functional electrical stimulation (FES), transcutaneous electrical nerve stimulation (TENS), temperature therapy stimulation, and deep vein thrombosis (DVT) prophylactic stimulation; and
   a control unit controlling the at least one actuator and the plurality of electrodes according to a coordinated sequence of the reciprocating motion and transmission of the tour modalities;
   wherein the control unit comprises:
   a microcontroller,
   an input unit for programming and adjusting the coordinated sequence into the microcontroller;
   a neuromuscular feedback component for adjusting the FES modality according to a response in the muscles and the coordinated sequence;
   a neurofeedback mechanism for adjusting the TENS modality according to an activity of nerves in the limb and the coordinated sequence; and
   a biomechanical component for monitoring and analyzing a biomechanical response and range of motion of the joint and for adjusting one or more of the four modalities according to the biomechanical response and the coordinated sequence; and
   wherein each of the plurality of electrodes comprises:
   a signal generator for supplying an electrical current needed to generate the four modalities according to the coordinated sequence;
   a transmission layer for receiving the electrical current and providing one of the four modalities;
   a temperature unit configured to be in contact with the limb, the temperature unit being adapted to receive the electrical current, provide the temperature therapy stimulation, and monitor a temperature of the temperature unit and a temperature of the limb; and
   further comprising at least one electrode having a detection layer for monitoring venous blood flow and pain experienced in the patient, wherein the detection layer comprises an ultrasound Doppler for measuring a blood flow in the limb and communicating the blood flow measurement to the control unit, the control unit adjusting the coordinated sequence to effect a desirable blood flow.

2. The apparatus of claim 1, wherein the reciprocating motion involves the at least one actuator cyclically disposing the at least one support member between an extension position causing the limb to stretch and a flexion position causing the limb to bend.

3. The apparatus of claim 2, wherein the at least one actuator provides for a uniform speed during successive cycles of the reciprocating motion.

4. The apparatus of claim 2, wherein the at least one actuator provides for variable speed between successive cycles of the reciprocating motion.

5. The apparatus of claim 1, wherein the apparatus further comprises at least one sensor for determining a status of the reciprocating motion and providing sensing signals representative thereof to the control unit, the status of the reciprocating motion comprising a speed of the reciprocating motion and a position in which the at least one support member is disposed.

6. The apparatus of claim 1, further comprising a first conductor having a proximal end connected to the control unit and a distal end connected to the actuator, and at least on second conductor having a proximal end connected to the control unit and a distal end connected to at least one of the plurality of electrodes;

wherein the first and second conductors establish Communication between the control unit, actuator, and electrodes.

7. The apparatus of claim 1, wherein the control unit, actuator, and each of the plurality of electrodes each have a transmitter-receiver unit for providing wireless communication between the control unit, actuator, and electrodes.

8. The apparatus of claim 1, wherein the temperature unit provides heat to the limb.

9. The apparatus of claim 1, wherein the temperature unit provides cooling to the limb.

10. The apparatus of claim 1, wherein the detection layer continuously measures a pain level in the limb and communicates the pain level to the control unit, the control unit administering a pain medication to the patient through an analgesia pump to reduce the pain level.

11. The apparatus of claim 1, wherein a compression unit includes at least one of the plurality of electrodes for providing the DVT prophylactic stimulation, the compression unit being adapted to receive the electrical current from the signal generator and apply a pressure modulation to the limb.

12. The apparatus of claim 1 wherein the plurality of electrodes further transmit at least one modality chosen from the group consisting of venous blood flow monitoring and pain monitoring.

13. The apparatus of claim 1 wherein the plurality of electrodes further transmit two modalities comprising venous blood flow monitoring and pain monitoring.

14. The apparatus of clam 1, wherein the control unit includes a plurality of user accounts, said user accounts having varying levels of control in programming said coordinated sequence of the reciprocating motion and transmission of the four modalities.

15. The apparatus of claim 14, the user accounts comprise a patient account for the patient and a healthcare professional account for a healthcare professional, said healthcare professional account providing a complete control in programming said coordinated sequence of the reciprocating motion and transmission of the four modalities.

16. The apparatus of claim 15, wherein the healthcare professional account provides for defining a level of control for the patient account, the level of control being equal to the complete control.

17. The apparatus of claim 15, wherein the healthcare professional account provides for defining a level of control for the patient account, the level of control being limited according to one or more restrictions set by the healthcare professional.

18. A non-invasive apparatus for rehabilitating a joint, limb, muscles of a patient recovering from surgery on the joint, the apparatus comprising:

a continuous passive motion (CPM) device haying a frame, at least one support member for supporting and securing the limb to the frame, at least one hinge coupled to the at least one support member, and at least one actuator for providing reciprocating motion of the at least one support member about the at least one hinge;

a sleeve adapted to fit over and conform to the joint and limb and provide or a full range of motion of the limb;

a plurality of electrodes disposed on the sleeve, wherein the plurality of electrodes transmit at least four modalities to the patient for stimulation, the at least four modalities chosen from a group consisting of functional electrical stimulation (FES), transcutaneous electrical nerve stimulation (TENS), temperature therapy stimulation, deep vein thrombosis (DVT) prophylactic stimulation, venous blood flow monitoring, and pain monitoring;

a control unit controlling the at least one actuator and the plurality of electrodes according to a coordinated sequence of the reciprocating motion and transmission of the at least four modalities; and at least one sensor disposed on the at least one support member for determining a status of the reciprocating motion and providing sensing signals representative thereof to the control unit;

wherein the control unit comprises:

a microcontroller, an input unit for programming and adjusting the coordinated sequence into the microcontroller;

a neuromuscular feedback component for adjusting the FES modality according to a response in the muscles and the coordinated sequence;

a neurofeedback mechanism for adjusting the TENS modality according to an activity of nerves in the limb and the coordinated sequence; and a biomechanical component for monitoring and analyzing a biomechanical response and range of motion of the joint and for adjusting one or more of the at least four modalities according to the biomechanical response and the coordinated sequence; and wherein each of the plurality of electrodes comprises:

a signal generator for supplying an electrical current needed to generate the four modalities according to the coordinated sequence;

a transmission layer for receiving the electrical current and providing one of the four modalities;

a temperature unit configured to be in contact with the limb, the temperature unit being adapted to receive the electrical current, provide the temperature therapy stimulation, and monitor a temperature of the temperature unit and a temperature of the limb; and further comprising at least one electrode having a detection layer for monitoring venous blood flow and pain experienced in the patient, wherein the detection layer comprises an ultrasound Doppler for measuring a blood flow in the limb and communicating the blood flow measurement to the control unit, the control unit adjusting the coordinated sequence to effect a desirable blood flow.

19. The apparatus of claim 18, wherein the sleeve includes one or more sleeve fasteners adapted to secure the sleeve to the limb and ensure a direct contact between the limb and each of the electrodes.

20. The apparatus of claim 18, wherein the sleeve includes one or more attachments adapted to provide a releasable engagement between the CPM device and the sleeve and provide additional support to the limb; and wherein the sleeve can still be used without being engaged with the CPM device and the CPM device can be used without removing the sleeve from the limb.

21. The apparatus of claim 18, wherein the sleeve comprises an elastic material providing constant contact with the limb and joint while providing flexibility for the full range of motion of the limb.

22. The apparatus of claim 18, wherein the detection layer continuously measures a pain level in the patient's limb and communicates the pain level to the control unit, the control unit administering a pain medication to the patient through an analgesia pump to reduce the pain level.

23. The apparatus of claim 18, wherein one or more of the plurality of electrodes includes a compression unit for providing the DVT prophylactic stimulation, the compression unit being disposed on the sleeve and adapted to receive the electrical current from the signal generator and apply a pressure modulation to the limb.

24. The apparatus of claim 18, wherein the control unit includes a plurality of user accounts, said user accounts having varying levels of control in programming said coordinated sequence of the reciprocating motion and transmission of the at least tour modalities.

25. The apparatus of claim 18, wherein the coordinated sequence is configured to simultaneously transmit reciprocating motion of the CPM device and a first, second, third, and fourth modalities of the at least four modalities by a first, second, third, and fourth groups of the plurality of electrodes, respectively.

26. A non-invasive apparatus for rehabilitating a joint, limb, and muscles of a patient recovering from surgery on the joint, the apparatus comprising
- a continuous passive motion (CPM) device having a frame, at least one support member for supporting and securing the limb to the frame, at least one hinge coupled to the at least one support member, and at least one actuator for providing reciprocating motion of the at least one support member about the at least one hinge;
- a sleeve adapted to fit over and conform to the joint and limb and provide for a full range of motion of the limb;
- a plurality of electrodes disposed on the sleeve, wherein the plurality of electrodes transmit a plurality of modalities to the patient for stimulation, the plurality of modalities being functional electrical stimulation (FES), transcutaneous electrical nerve stimulation (FENS), temperature therapy stimulation, deep vein thrombosis (DVT) prophylactic stimulation, venous blood flow monitoring, and pain monitoring;
- a control unit controlling the at least one actuator and the plurality of electrodes according to a coordinated sequence of the reciprocating motion and transmission of the plurality of modalities; and
- at least one sensor disposed on the at least one support member for determining a status of the reciprocating motion and providing sensing signals representative thereof to the control unit;
- wherein the control unit comprises:
- a microcontroller,
- an input unit for programming and adjusting the coordinated sequence into the microcontrollers;
- a neuromuscular feedback component for adjusting the FES modality according to a response in the muscles and the coordinated sequence;
- a neurofeedback mechanism for adjusting the TENS modality according to an activity of nerves in the limb and the coordinated sequence; and
- a biomechanical component for monitoring and analyzing a biomechanical response and range of motion of the joint and for adjusting one or more of the four modalities according to the biomechanical response and the coordinated sequence; and
- wherein each of the plurality of electrodes comprises:
- a signal generator for supplying an electrical current needed to generate the four modalities according to the coordinated sequence;
- a transmission layer for receiving the electrical current and providing one of the four modalities;
- a temperature unit configured to be in contact with the limb, the temperature unit being adapted to receive the electrical current, provide the temperature therapy stimulation, and monitor a temperature of the temperature unit and a temperature of the limb; and
- further comprising at least one electrode having a detection layer for monitoring venous blood flow and pain experienced in the patient, wherein the detection layer comprises an ultrasound Doppler for measuring a blood flow in the limb and communicating the blood flow measurement to the control unit, the control unit adjusting the coordinated sequence to effect a desirable blood flow.

27. The apparatus of claim 26, wherein the sleeve comprises an elastic material providing constant contact with the limb and joint while providing flexibility for the full range of motion of the limb and includes one or more attachments adapted to provide a releasable engagement between the CPM device and the sleeve.

28. The apparatus of claim 26, wherein a compression unit includes one of the plurality of electrodes for providing the DVT prophylactic stimulation, the compression unit being adapted to receive the electrical current from the signal generator and apply a pressure modulation to the limb.

29. The apparatus of claim 26, wherein the device can be used in a preoperative setting to optimize an outcome of the surgery and in a general rehabilitation setting to address a de-conditioning, loss of function, and loss of full range of motion in the limb.

* * * * *